United States Patent [19]
Budowsky et al.

[11] Patent Number: 5,962,431
[45] Date of Patent: *Oct. 5, 1999

[54] METHOD OF TREATING PAPILLOMAVIRUS USING 2',5'-OLIGOADENYLATE

[76] Inventors: Edward I. Budowsky, 2752 Middleton Ave., Apt. 28B, Durham, N.C. 27705; Alexander E. Gavrilov, Novolesnaya ul. 17A, Apt. 82, Moscow, Russian Federation, 103055; Arman D. Pivasyan, 132 Lawrence St., New Haven, Conn. 06511

[ * ] Notice: This patent issued on a continued prosecution application filed under 37 CFR 1.53(d), and is subject to the twenty year patent term provisions of 35 U.S.C. 154(a)(2).

[21] Appl. No.: 08/979,926

[22] Filed: Nov. 26, 1997

Related U.S. Application Data

[62] Division of application No. 08/615,246, filed as application No. PCT/EP93/02596, Sep. 24, 1993, Pat. No. 5,739,013.

[51] Int. Cl.$^6$ ............... A01N 43/04; C07H 19/00; C12N 9/22
[52] U.S. Cl. ............... 514/46; 536/22.1; 435/91.1
[58] Field of Search ............... 435/91.1, 199; 514/44, 45, 46, 47; 536/22.1, 23.2

[56] References Cited

U.S. PATENT DOCUMENTS

| | | | |
|---|---|---|---|
| 4,378,352 | 3/1983 | Kimchi et al. | 514/47 |
| 4,859,768 | 8/1989 | Suhadolnik et al. | 536/27 |
| 5,550,111 | 8/1996 | Suhadolnik et al. | 514/44 |
| 5,739,013 | 4/1998 | Budowsky | 435/91.1 |

FOREIGN PATENT DOCUMENTS 4211238 10/1993 Germany .

*Primary Examiner*—Jon P. Weber
*Assistant Examiner*—Susan Hanley
*Attorney, Agent, or Firm*—Foley & Lardner

[57] ABSTRACT

A method for treating diseases and symptoms caused by papillomaviruses is presented. The method comprises administering an effective amount of one or more 2',5'-oligoadenylates consisting of the structure:

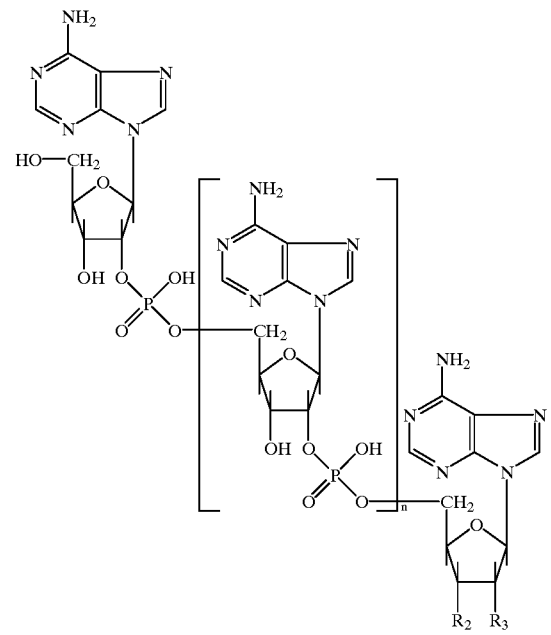

wherein $R_2$ is $PO_4^{2-}$ and $R_3$ is OH, $R_2$ and $R_3$ are OH; and n=1 or n=2.

3 Claims, 2 Drawing Sheets

METHOD OF TREATING PAPILLOMAVIRUS USING 2',5'-OLIGOADENYLATE

This application is a divisional, of application Ser. No. 08/615,246, filed Nov. 21, 1996, now U.S. Pat. No. 5,739,013, which is National Phase of PCT/EP93/02596 filed Sep. 24, 1993.

BACKGROUND

The invention relates to 2',5'-oligoadenylates which possess a cyclophosphate group at the 3' end and a free OH group at the 5' end, to a process for preparing these compounds, to a pharmaceutical preparation comprising them, and to the use of these compounds for treating external papillomatoses.

The invention relates to novel chemical compounds, specifically 2',5'-oligoadenylate-2',3'-cyclophosphates of the general formula

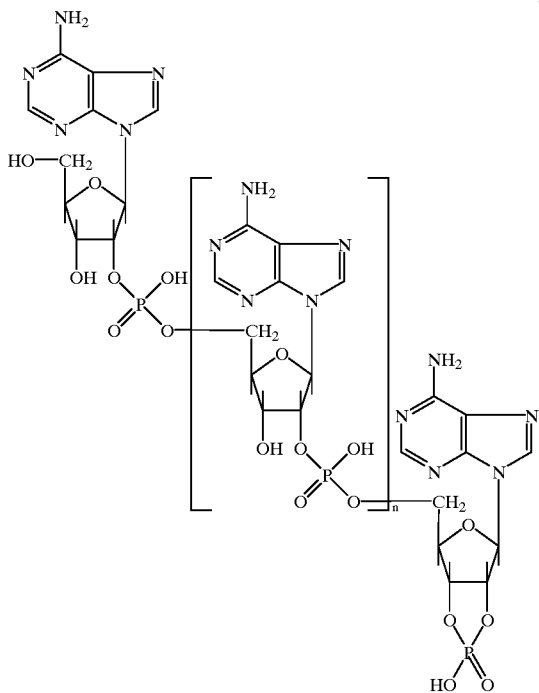

I in which $0 \leq n \leq 10$, in particular from $\geq 0$ to 10, preferably 1 or 2.

The compounds in which n=1 or 2, in particular, may advantageously be used for medicinal purposes, specifically for the topical treatment of dermal and epithelial lesions which are caused by papilloma viruses.

Papillomatoses which are caused by papilloma viruses of the Papovaviridae family are infectious diseases which are widely distributed in humans and animals. Currently, more than 60 types of human papilloma viruses are known.

All these viruses possess a similar structure. In each case, their genome consists of a double-stranded, covalently closed annular DNA of 8000 base pairs which encodes the virion proteins and the proteins which are required for the intercellular development of the virus. In the infected cell, the papilloma virus genome is replicated over many generations in the form of episomes (dozens of copies per cell). Mature virions are only formed in the cells at the final stage of differentiation.

Under persistent conditions, it is only the first genes of the papilloma virus genome which are expressed, with these genes causing an alteration in the cell phenotype and in this way leading to the formation of papillomatoses. In the infected cells, a particular moiety of the virus genome has a probability, which is dependent on the virus type and on other factors, of being able to be incorporated into the cell genome, something which can then trigger conversion to malignancy. It is known that a substantial number of human tumors are the result of the conversion of papillomatoses to malignancy. These tumors thus represent a consequence of persistent, latent viral infections.

In this context, anogenital papillomatoses which are transferred by the sexual route are the most dangerous as far as conversion to malignancy is concerned (see M. Spitzer, Obstet. Gynecol., 1989, vol. 73, N3, pp. 303–307; H. zur Hausen, A. Schneider, The Role of Papilloma viruses in Human Anogenital Cancer, in: The apapovaviridae (N. P. Alzman ed.), 1987, vol. 2, pp. 245–263; H. zur Hausen, Papilloma viruses as Carcinomaviruses, in: Adv. in Virus Oncology (G. Klein ed.), 1989, vol. 8, pp. 1–26).

Since papillomatoses are precancerous disorders which are easy to diagnose, the development of many tumors can be prevented by treating benign papillomatoses, i.e. before malignant conversion of the infected cells takes place.

At present, the most important methods for treating papillomatoses are surgical removal of the papillomas and necrotization by means of electrocauterization, cryocauterization or laser cauterization (see Virus infections. Etiology, epidemiology, clinics, pathogenesis and diagnosis. Rep. Col. of Scient. Public., Sverdlovsk, 1985 (in Russian)). For this purpose, use is made of liquid oxygen, and acids and mixtures thereof (nitric acid, oxalic acid, lactic acid, etc.), which bring about necrosis of the surrounding healthy tissue and, at the application site, lead to scar formation and frequently to recurrences and to the appearance of new papillomas close to the site from which the old ones were removed (see S. A. Bashi, Cryoterapia versus podophyllin in the treatment of genital warts, Int. J. Dermatol., 1985, vol. 24, N 8, pp. 535–536).

The effectiveness of medicinal methods for treating papillomatoses using podophyllotoxin and interferon is low and is also associated with powerful side effects and/or after-effects, even when therapeutic doses are used.

The biological activity of podophyllin can be explained by its antimitotic effect, which is comparable to that of colchicin. Its use frequently causes local reactions (inflammations, allergic contact dermatoses, occasional skin erosions, etc.) and also undesirable after-effects such as peripheral neuropathy, tachypnea, hematuria and spontaneous abortion (see K. R. Beutner, Podophyllotoxin in the treatment of genital human papilloma virus infections. Seminars in Dermatology, 1987, vol. 6, NI, pp. 10–18).

In the case of papillomatoses, the administration of interferon has only a slight effect, and the doses which are employed for this treatment can lead to suppression of the immune system and to the triggering of autoimmune disorders (see F. G. Bruins, A. J. C, von don Brule, R. Mullnik, G. M. M. Walboomers, C. J. Meijer, R. Willemze, J. Invest. Dermatol., 1989, vol. 93, N4, pp. 544–545; M. Foldvan, A. Moreland, M. Nezei, ibid., pp. 550; G. Gross, Roussaki, ibid., pp. 553; M. Niimura, imbid., pp. 567).

Synthetic analogs of 2',5'-oligoadenylates (2,5 A) are known for the fact that they exhibit immunosuppressant activity and have previously been proposed for use in surgical transplantation. It has been established that oligoadenylates are less toxic, more specifically active and more effective, as mediators of the effects caused by interferon, than are immunosuppressants (see A. Kimchi et al., U.S. Pat. No. 4,378,352 (1983)).

The same effect is also achieved by a synthetic 2,5 A which contains a terminal morpholine group (see R. Torrence et al., U.S. Pat. No. 4,515,781 (1985)).

2,5 A analogs which possess at least three adenosine fragments are known to be active inhibitors of viral protein synthesis in vitro (see Jan M. Kerr et al., U.S. Pat. No. 4,21,P,746 (1980)).

While some synthetic analogs of 2,5 A-oligo-3'-deoxyadenylates and their derivatives inhibit the infection and transformation of animal cells with herpes simplex and Epstein-Barr viruses, in particular in in-vitro cultures, they are nevertheless inactive in the case of cells which are already infected or transformed (see R. I. Suhadolnik et al., U.S. Pat. No. 4,464,359 (1984); R. I. Suhadolnik et al., U.S. Pat. No. 4,539,313 (1985); R. I. Suhadolnik et al., U.S. Pat. No. 4,708,935 (1987)).

It is possible to use 2,5 A for treating infectious diseases which are caused by cytomegalovirus, hepatitis B virus and varicella zoster viruses (see European Patent Application No. 121 635 (Au, No. J, Dk, Fi, Fr, Es), 1984).

SUMMARY OF THE INVENTION

The object of the invention is to make available an effective pharmaceutical having a selective effect for the treatment of cutaneous and epithelial lesions which are caused by papilloma viruses.

The object of the invention is achieved by the provision of 2',5'-oligoadenylate-2',3'-cyclophosphates of the formula I

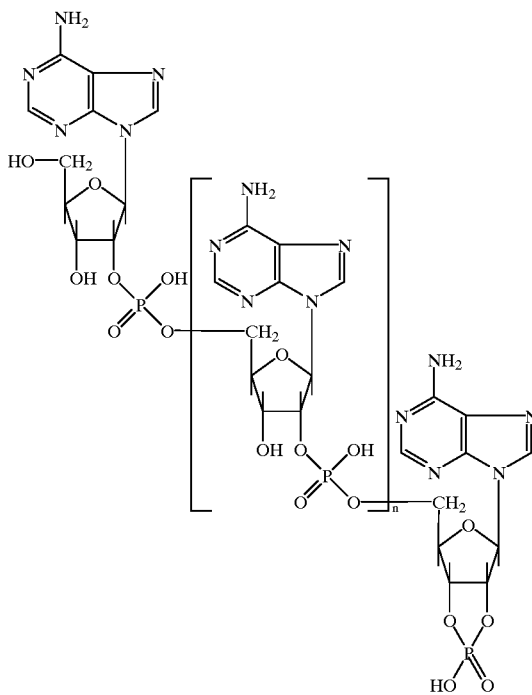

in which $0 \leq n \leq 10$, in particular from $\geq 0$ to 10, preferably 1 or 2.

The invention also relates to processes, proceeding from poly(A), for preparing the novel compounds, an described in detail below.

DETAILED DESCRIPTION OF THE INVENTION

Figure 1:
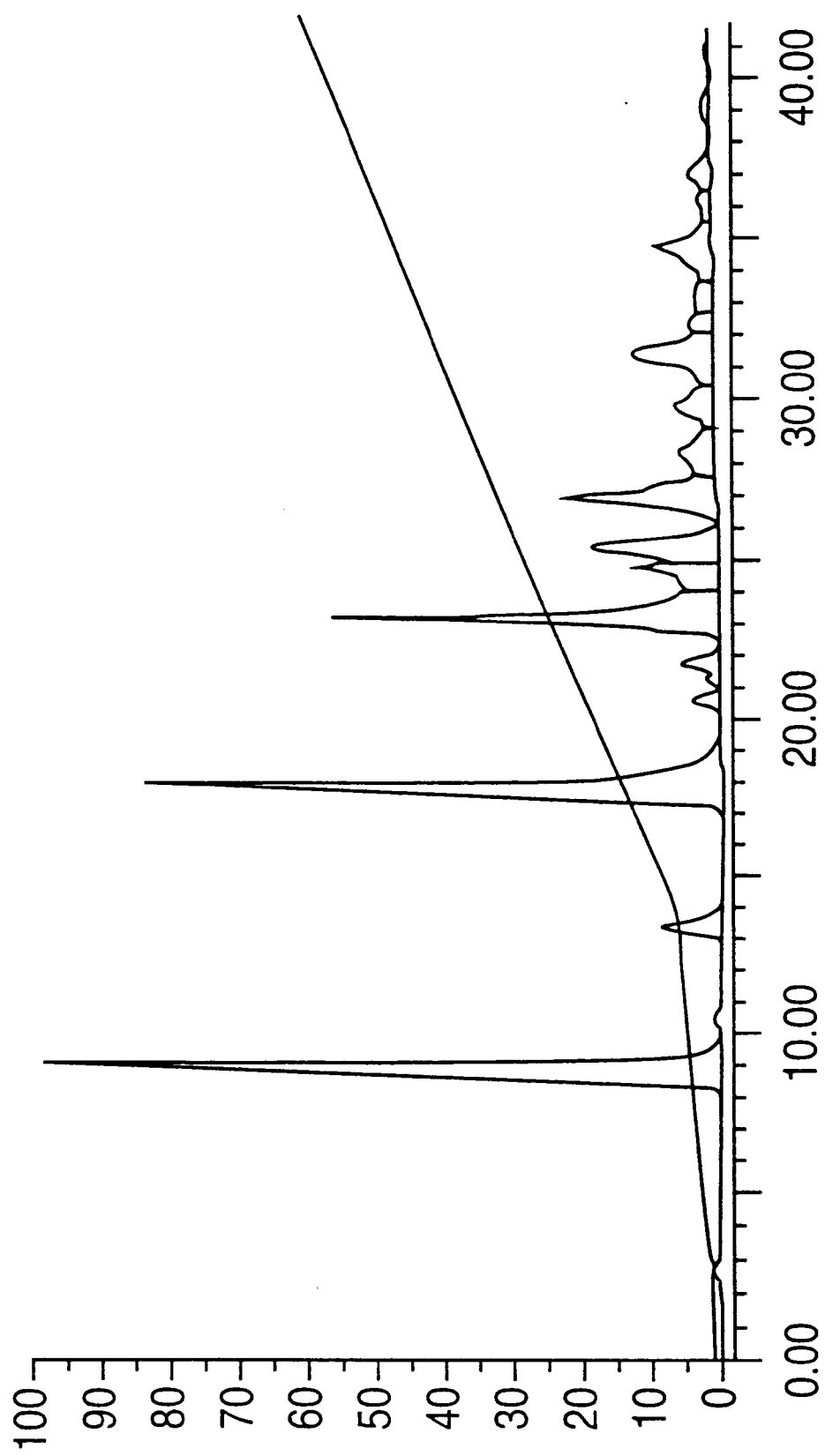
FIG. 1:
HPLC analysis of mixture A (2',5'-oligoadenylate-2',3'-cyclophosphates). Column: Diasorb $NH_2$, 4×150 mm.
Mobile phase: A—20% $CH_3OH$; B=2M $AcONH_4$ in 20% $CH_3OH$.
Flow rate: 0.7 ml/min; 0'-2'—1% B, 2'-14'—0.5% B/min, 14'-50'—2% B/min.
Detection at 260 nm. Composition of the mixture corresponding to the absorption at 260 nm: 23% monomer (8.7 min), 22.5% dimer (17.5 min), 14% trimer (23 min), 6.8% tetramer (26.8 min).

These compounds may be prepared in a manner known per se from poly(A) having irregular 2',5' and 3',5' internucleotide bonds in accordance with a known process (see A. M. Michelson: In the Chemistry of the Nucleosides and Nucleotides (Academic Press) 1963, pp. 418 and 419) by means of the chemical polymerization of 2'(3')-adenosine monophosphate. The subsequent cleavage of the 3',5' bonds in this polymer with B. intermedius ribonuclease (E.C.3.1.4.23) leads to a mixture containing monomers and 2',5'-oligoadenylates of differing length and possessing terminal 2',3'-cyclophosphate groups.

The same results are also obtained using another two-stage process:
1. Cleaving the poly(A) with T2 ribonuclease (or similar ribonucleases), resulting in a series of 2',5'-oligoadenylates, with each oligomer constituting a mixture of 2',3'-cyclophosphate and 3'-monophosphate, and
2. treating this mixture with a 100-fold excess of BrCN in buffered aqueous solution, resulting in the conversion of the terminal 3'-phosphate group into the 2',3'-cyclophosphate group.

These two synthesis routes may be depicted diagrammatically as follows:

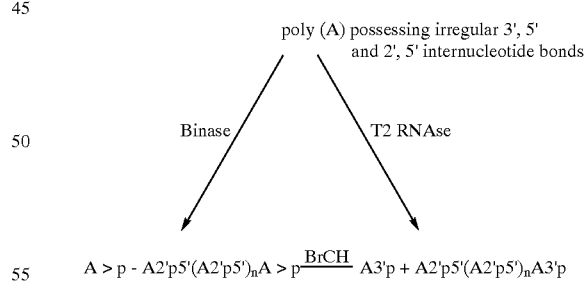

The resulting mixtures of 2',5'-oligoadenylates are analyzed and the desired oligonucleotides in accordance with formula I are purified by HPLC.

There has hitherto been no report of 2',5'-oligoadenylates having a terminal 2',3'-cyclophosphate group as individual compounds. Both the 2'(3')-phosphate groups and the 2',3'-cyclophosphate groups in the 2',5'-oligoadenylates effectively prevent the hydrolysis of these compounds by cell enzymes. The efficacy of the 2',3'-cyclophosphate analogs as compared with the natural 2',5'-oligoadenylates containing the 5'-triphosphate group is explained by their greater ability to permeate cells due to their lower charge and their resistance towards hydrolysis by phosphodiesterases together with cell enzymes.

The novel 2',5'-oligoadenylates are dissolved in water or aqueous solutions of neutral salts and applied once or twice daily to the dermal lesions (ordinary plane warts and plantar warts, condylomas, etc.) for 2 weeks. The active compound concentration is from $10^{-4}$ to $10^{-7}$ M.

As a result of their having been treated, the condylomas stop growing and no new growth takes place; in most cases, the old condylomas remit within from 4 to 6 weeks.

In the case of ordinary warts, the papules become flatter towards the end of the first week and disappear completely from 2 to 4 weeks after the beginning of the treatment. Patients suffering from plane warts are completely cured 1 month after beginning the treatment.

During the treatment of papillomas, the new growths shrink, and smaller papillomas are sloughed off, after 1.5 to 2 weeks and there is complete retrogression of the dermal lesions within 1 month. In not one single case is there any scar formation. Nor is the healing process accompanied by toxic/allergic reactions or other side effects.

While the concentration of the active oligoadenylates in the treatment solutions is at least two orders of magnitude higher than in the case of the interferon-induced cells, the total quantity of solution which is applied is, however, normally less than 1.0 ml. Therefore, even if all the oligoadenylates are absorbed, the average concentration in the cells and body fluids (blood, urine, etc.) is far below that in the non-induced cells. The concentration of the applied compounds can only transiently (immediately after treatment) be higher than that of their natural analogs in the normal cells and then only in the tissues in the immediate vicinity of the application site.

The 2',5'-oligoadenylates can be readily degraded by nucleases and phosphatases which are present within and outside the cells of the organism. Adenylic acid and adenosine, which constitute customary cell metabolites whose average concentration in the cells is less than $10^{-3}$ M, are then formed as end products.

Both individual oligonucleotides of the formula I and mixtures which contain them can be used for treating dermal and epithelial lesions which are induced by papilloma viruses.

The topical use of small doses of the novel 2',5'-oligoadenylates for treating papillomatoses is extremely effective, with no negative dermal reactions, nor any systemic side effects, being observed. In more than 80% of patients, treatment of lesions results in complete retrogression. No recurrences are observed after an observation period of 3 months.

The novel preparation may be administered in various formulations which are acceptable for topical use. These formulations are prepared by the careful mixing or dissolution of the individual compounds, or their mixtures, with a pharmaceutically acceptable excipient using the customary techniques, with it being possible for the excipient to have very widely differing forms depending on the formulation of the preparation which is desired for the application, i.e. on the outer skin or on mucosal tissues. A very wide variety of pharmaceutical media, for example liquid excipients such as water, dimethyl sulfoxide in the presence or absence of alcohols, glycols, etc., or in the form of a pomatum, an ointment or a plaster, may be used for producing the preparations. It is particularly advantageous to formulate the abovementioned pharmaceutical preparations in a unit dose form in order to facilitate and simplify dosage. The expression "unit dose form" refers to physically discrete units each of which contains a specific quantity of active compound, which quantity is so calculated as to achieve, in combination with the requisite pharmaceutical excipient, the desired therapeutic effect. The appropriate dose for a single use for treating papillomatoses should be from $10^{-9}$ to $10^{-8}$ mol of active compound (n=1 and/or 2) per papule (from 3 to 5 mm in diameter). The total duration of the treatment is up to 30 days, with the preparation being administered daily.

EXAMPLES

The following examples illustrate the preparation of oligonucleotide mixtures and individual 2',5'-oligoadenylates. Chemicoenzymic synthesis, purification and analysis of the 2',5'-oligoadenylates.

All the reactions are carried out at room temperature.

a) Synthesis of poly(A):

0.9 g (2.5 mmol) of adenosine-2'(3')-monophosphate in $H^+$ form and 1.2 ml (2.6 mmol) of tri-n-octylamine are dissolved in 30 ml of methanol/ethanol (1:1), with the solution being stirred for several hours. After that, the insoluble constituents are filtered off using a glass filter, after which the filtrate is evaporated to dryness using a rotary evaporator. The resulting solid is then dissolved in 10 ml of abs. dioxane and evaporated to dryness using a rotary evaporator. Both procedures are repeated twice. The resulting solid is then dissolved in 5 ml of abs. dioxane, after which 0.77 ml (3.75 mmol) of diphenylphosphoryl chloride are added dropwise while stirring with a magnetic stirrer. 3.3 ml (7.5 mmol) of tri-n-octylamine are then added. The resulting solution is then stirred for 1 hour, after which 0.77 ml of diphenylphosphoryl chloride and 3.2 ml of tri-n-octylamine are added and the mixture is stirred for a further 4 hours. The reaction mixture is then poured, while stirring, into 5 vol. of hexane/ether (4:6). The precipitate is then filtered off using a glass filter, washed with the abovementioned mixture and then with ether, and dried in vacuo. In this way, a white powder of polyadenylate possessing irregular 2',5' and 3',5' internucleotide bonds is obtained. The general formula of the mixture is $(A2'(3')P-)_n$ A>p, in which n=10.

The dry polymer mixture is dissolved in 12 ml of water by adjusting the pH to 9.3 by means of adding conc. ammonia solution. After that, 3 vol. of ethanol are added, with the pH then being adjusted to 3.0 with 5 M HCl. The precipitate which is formed after keeping the mixture at $-18°$ C. is centrifuged off, washed with 75% ethanol and dried in a current of air. A substantial proportion of the monomer remains in the supernatant.

b) Selective cleavage of the 3',5' internucleotide bonds by means of cleaving with binase The precipitate which is obtained in a) in dissolved in 40 ml of $H_2O$, with the pH being adjusted to 7.0 using a 3 M solution of tris base; after that, 2 ml of a solution of Bacillus intermedius RNAse (binase, E.C.3.1.4.23) (150 U/mg) are added and the mixture is then stirred for 10 to 12 hours. After that, the enzyme is extracted by extraction with the same volume of chloroform/isoamyl alcohol (24:1). The resulting aqueous phase contains a mixture of 2',3'-cyclophosphates of adenosine and 2',5'-oligoadenylates.

c) Isolation of the individual compounds

Preliminary separation of the individual components is effected by means of ion exchange chromatography using DEAE Spheron 1000 in the $HCO_3$ form (16×600 mm, 120 ml). Following deproteinization, the product obtained from the enzymic cleavage of poly(A) is concentrated by being subjected to rotary evaporation approximately 8 to 10 times and is then, after 10 vol. of ethanol have been added, kept at −18° C. for 12 hours. Following centrifugation (3000 rpm for 10 to 20 min), the precipitate is dissolved in water and loaded onto the column (optical density from 25,000 to 50,000 U at 260 nm). After the column has been washed with water and with 0.05 M triethylammonium bicarbonate (pH 8.0), the products are eluted using a linear gradient of this salt (from 0.1 to 0.8 M, total volume 1 L). The fractions which contain the enriched individual compounds are then evaporated to dryness on a rotary evaporator and lyophilized in order to remove the buffer components completely.

Figure 2A:
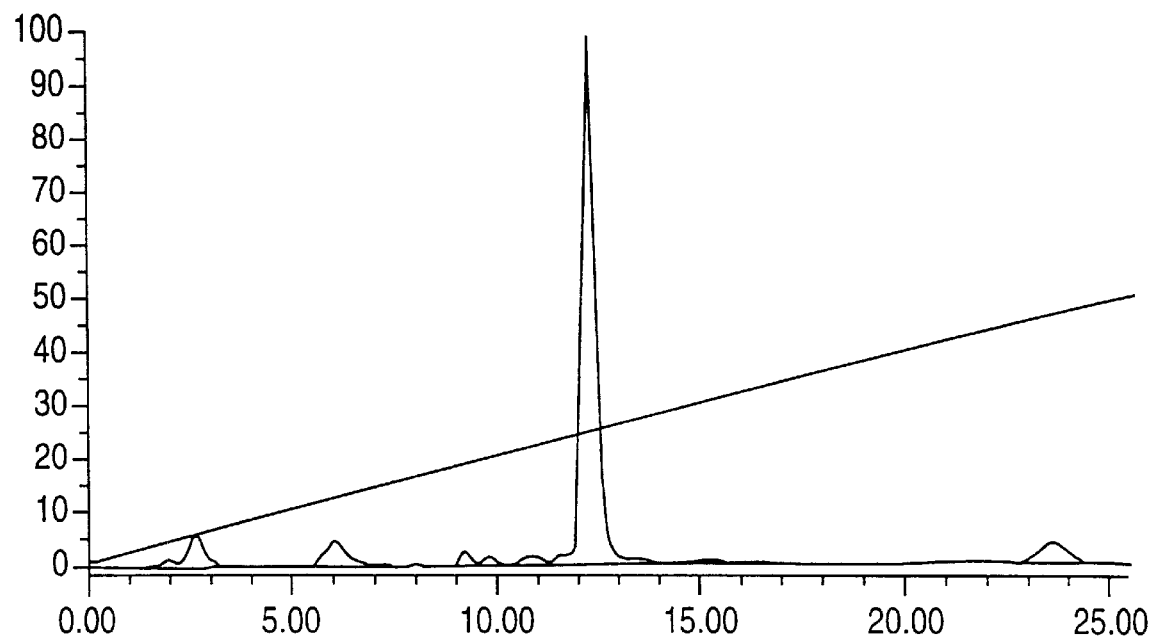
FIG. 2:
HPLC analysis of the purified 2',5'-trimer-(A)- and tetramer-(B)-2',3'-cyclophosphates.
Column, composition of the mobile phase and flow rate as in FIG. 1, gradient—2% B/min.
Figure 2B:
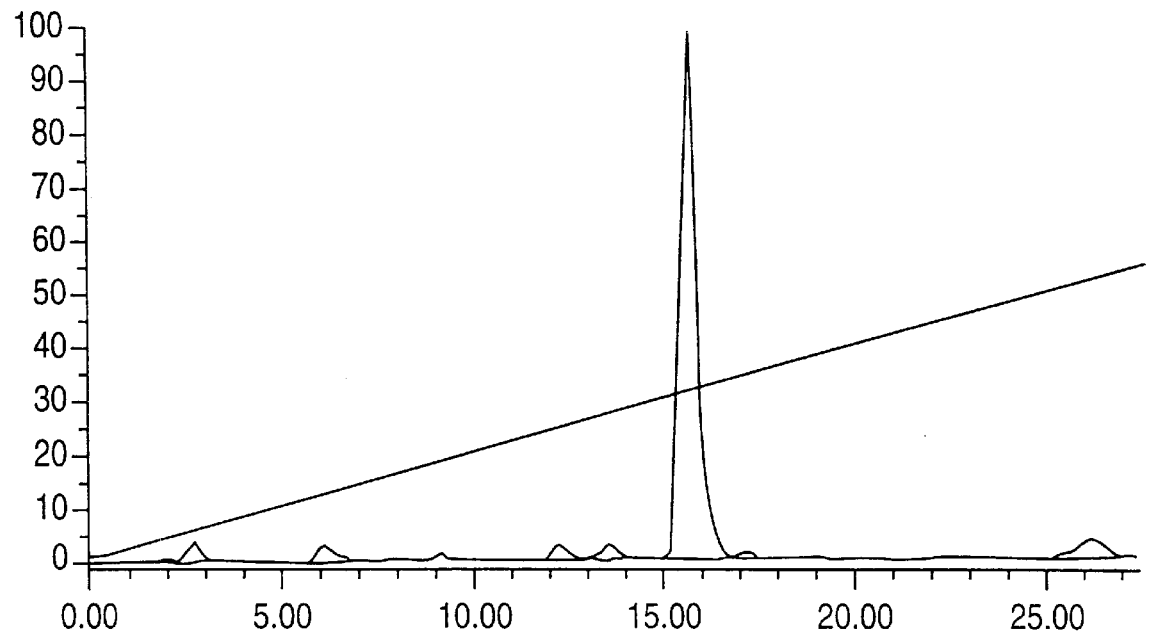

The final purification of the individual compounds is effected by HPLC, as described below (loading of the semipreparative column with approx. 2000 U optical density). The desalting of the solution after the HPLC is effected by sorbing a 10- to 20-fold diluted solution onto small DEAE columns after washing with water, eluting with a small volume of 1 M triethylammonium bicarbonate and lyophilizing the solution.

d) Purification and analysis of the 2',5'-oligoadenylates by means of HPLC chromatography The ion exchange chromatography is carried out on an $NH_2$-Diasorb column (8 μm, 4×150 mm for the analysis and 10 μm, 9.2×250 mm for the final preparative purification); linear gradient: eluent A—20% MeOH; B—2M AmAc, 20% MeOH, 2% B per mixture; flow rate—0.7 ml/min for the analytical column and 4 ml/min for the preparative column (FIGS. 1 to 3). Detection is effected using a UV monitor at 260 nm.

On the basis of the optical density at 260 nm, the mixtures contain 40 to 50% monomer, approx. 20 to 30% diadenylate, approx. 5 to 15% triadenylate, 2 to 8% tetraadenylate and 2 to 7% higher oligoadenylates. The mean molar extinction coefficient was $15 \cdot 10^3$ per adenosine residue, $36.8 \cdot 10^3$ for the trimer and $45.8 \cdot 10^3$ for the tetramer.

e) Determination of the composition of the individual compounds.

Each compound was kept at pH 1.0 (for 1 hour at 37° C.) in order to open the cyclophosphate group, after which it was dephosphorylated with bacterial alkaline phosphatase and subjected to alkaline hydrolysis of the internucleotide bonds (0.3 M NaOH, for 48 hours at 20° C.). The ratio of the end products (adenosine to adenosine-2'(3')-phosphate) was determined by HPLC. The results which were obtained in this context agree well with those which were predicted: Ado:AMP=1:1 for the dimer, 1:2 for the trimer and 1:3 for the tetramer. The standard error was less than 5%. On the basis of their HPLC mobility and NMR spectra ($^{31}P$ and $^1H$) the compounds resulting from the acid opening of the 2',3'-cyclophosphate group were identical to the known 2'(3')-phosphates of the corresponding oligoadenylates. On the other hand, the 2'(3')-phosphates which were obtained are converted quantitatively, in aqueous solution and at room temperature, into the starting 2',3'-cyclophosphates of the corresponding oligoadenylates by the action of BrCN (100-fold molar excess).

f) Elucidation of the type of internucleotide bond

Treatment of the 2',3'-cyclophosphates of the individual 2',5'-oligoadenylates with fresh binase under conditions which lead to complete cleavage into polyadenylic acid—adenosine—2',3'-cyclophosphate, does not result in any change in the HPLC separation profile and in the $^{31}P$ NMR spectra.

The only peaks to be observed in the $^{31}P$ NMR spectra were those corresponding to the terminal cyclophosphate group (20 to 21 ppm) and the 2',5'-internucleotide phosphate (0.02 to 0.4 ppm), at a ratio of 1:1 for the dimer, 1:2 for the trimer and 1:3 for the tetramer. The standard error was less than 2%. The 3',5' bond (less than 1% of internucleotide phosphate) was only detected in the case of the tetramer.

The oligoadenylates are colorless compounds and are readily soluble in water (up to $10^{-2}$ M), dimethyl sulfoxide, aqueous ethanol or glycerol. They are soluble in neutral, aqueous solution at 4° C. for several months and for an unlimited period in frozen solution (−20° C.) or in the lyophilized state.

Pharmacological Examples

Clinical investigation of the pharmaceutical preparation was carried out in papillomatosis patients. The patients were treated with the Na or triethylammonium salt of the corresponding compound, which had been diluted down to the requisite concentration with water or 0.1 M NaCl. The concentration of the active compound in the final solution was determined on the basis of the optical density of the solution at 260 an and using the abovementioned molar extinction coefficients. The results which were obtained in this context are summarized below. The examples merely illustrate the invention and do not limit it.

Example 1

Clinical trial of 2',5'-triadenylate-2',3'-cyclophosphate (n=1, AIII)

Diagnosis in the case of female patient M. (1958): sharp-edged condylomas. Findings: four condylomas (d=1 to 2 mm, h=2 to 8 mm) in the perineal region which were skin-colored, rough, elastic and sometimes painful. Accompanying illness: vaginitis.

Application of AIII ($10^{-4}$ M), at the daily rate of approx. 50 μl per condyloma. On the 4th day, all the condylomas exhibited a rugose surface and they had completely disappeared on the 8th day. No recurrences were observed after 8 weeks.

Diagnosis in the case of female patient P. (1950): multiple condylomas. Findings: 14 condylomas (d=2 to 8 mm, h=2 to 5 mm) in the perineal region which were elastic, skin-colored and sometimes painful.

Application of AIII ($10^{-4}$ M) for 2 weeks at the daily rate of 50 μl per condyloma. On the 6th day, all the condylomas had shrunk to half to one third of their initial size and, on the 10th day, 8 condylomas had disappeared completely without leaving any traces on the skin. The remaining 6 condylomas were still present and reassumed their original size 3 to 4 weeks after the treatment had been terminated. The treatment was not repeated. No changes were to be observed at 10 weeks after the end of the treatment (no recurrences and no formation of new condylomas).

Diagnosis in the case of female patient C (1958): plantar wart. Finding: a wart on the underside of the big toe (d=5 mm, h=3 mm) which was compact and of the same color as the surrounding tissue, and which had a rough surface and was very painful on walking.

Application of AIII ($10^{-4}$ M) at the daily rate of 50 μl per wart. On the 6th day, the wart had become softer and the surface of the wart could be rubbed off on mechanical manipulation. On the 10th day, the wart had completely disappeared and there was no longer any sensation of pain on walking. No recurrences were found on monitoring after 12 weeks. The relevant site on the skin surface did not differ in any way from the surrounding tissue.

Diagnosis in the case of patient C. (1926): papillomas. Findings: 7 papillomas were observed on the front and on the right-hand side of the neck, i.e. two large papillomas (d=3 and 2 mm, h=2.5 mm, dark brown) and 5 smaller papillomas (d=0.8 to 1.5 mm, 0.8 to 1.5 mm skin-colored). The papillomas appeared in 1982 during the menopause.

Application of AIII ($10^{-5}$ M) for 2 weeks at a daily rate of approx. 50 μl per papilloma. On the 5th day, the smaller papillomas had lost color and had shrunk and become flattened. No further changes could be observed. 2 to 3 weeks after the end of the treatment, the papillomas once again exhibited their original shape and size.

Example 2

Clinical trial of 2',5'-tetraadenylate-2',3'-cyclophosphate (n=2, AIV)

Diagnosis in the case of female patient S, 27 years of age: ordinary warts. Findings: three warts on the abdomen, 3 cm below the navel and of grayish color, prominent, diameter 2 to 3 mm. The warts were treated daily for two weeks with 1 to 3 drops of AIV ($10^{-5}$ M). On the 7th to 10th days after beginning the treatment, all the warts had shrunk and become flattened. One of the warts had completely disappeared at three weeks after the end of the treatment, as had the others at four weeks after the end of the treatment. There were no scar-like changes in the skin.

Seven further patients exhibiting multiple warts, i.e. exhibiting condylomas (six patients), ordinary warts (three patients) and unidentified warts (four patients), were treated daily for two weeks with an aqueous solution ($10^{-5}$ M) of AIV. The condylomas were located on the external genitalia and on the chest, with the warts being located on the wrists, on the body and on the legs.

In most cases, the condylomas and warts (in particular the former) shrank and became smaller after six to nine days of treatment. At 1 to 2 weeks after the end of the treatment, or during this period, three patients were already completely free of condylomas and two no longer exhibited any ordinary warts. At approx. 6 weeks after the end of the treatment, one patient was completely free of all six condylomas under the armpit. In two cases, the small condylomas (d<3 mm, 11 in all) on the external genitalia disappeared during or after the treatment, while the larger condylomas in the same region (d>5 mm, two in the first case and three in the second) regained their original size and form at 2 to 6 weeks after the treatment. While two of the six unidentified warts had disappeared at 2 to 3 weeks after treatment, the remainder did not show any reaction.

In not one single case were negative reactions, vestiges on the skin or recurrences observed during the treatment or for 8 to 12 weeks thereafter.

Example 3

Clinical trial of mixture A (mixture of 2',5'-oligoadenylate-2',3'-cyclophosphates, n≧0)

Two patients were tested, i.e. one exhibiting three ordinary warts (3 to 4 mm) on the neck, and a second exhibiting two pointed condylomas on the inner side of the leg. Each wart was moistened daily with 1 to 2 drops of a $10^{-4}$ M aqueous solution of mixture A. On the 9th day of treatment, all the ordinary warts had disappeared. A small condyloma disappeared after 7 days of treatment, while another disappeared three weeks after the end of the treatment, i.e. five weeks after beginning the treatment.

The results achieved clearly demonstrate the great efficacy of the investigated compounds and of the process for treating dermal and epithelial lesions caused by human papilloma viruses. In not one single case was the treatment of the papillomatoses with 2',5'-oligoadenylates accompanied by a painful or inflammatory reaction and a subjective or objective aggravation of the patient's condition.

The high clinical efficacy of the 2',5'-oligoadenylates at very low dosage, and the absence of local reactions and systemic side effects, and also the freedom from relapses, provide proof of the advantages of the said compounds for treating papillomatoses.

Similar results to those obtained in the treatment of papillomatoses were also achieved using previously known compounds, i.e. using 2',5'-oligoadenylates having natural adenosine residues and 2'(3')-phosphate groups (series B) or free 2'- and 3'-hydroxyl groups (series C) on the 3-terminal adenosine residue. In these cases, both the individual compounds, such as trimers and tetramers, or their mixtures with other oligomers: trimers B and C, tetramers B and C, mixtures B and C prove to be extremely effective in the treatment of external papillomatoses.

We claim:

1. A method for treating diseases and symptoms caused by papillomaviruses in a subject in need of such treatment comprising administering an effective amount of one or more 2',5'-oligoadenylates consisting of the structure:

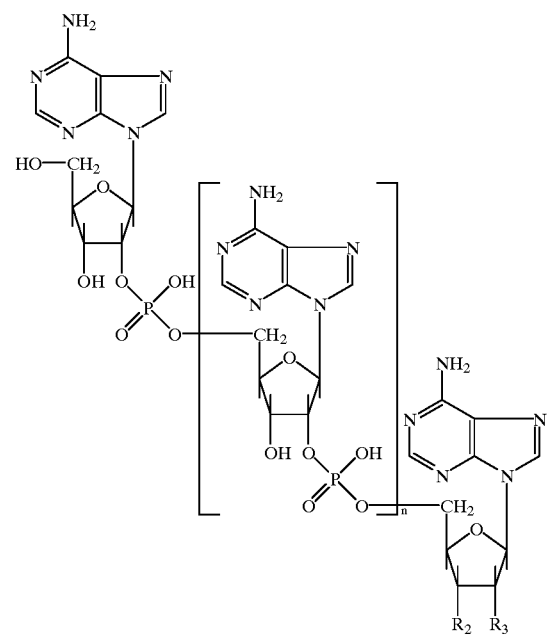

wherein $R_2$ is $PO_4^{2-}$ and $R_3$ is OH, $R_2$ and $R_3$ are OH; and n=1 or n=2.

2. The method for treating diseases and symptoms caused by papillomaviruses in a subject in need of such treatment comprising administering a pharmaceutically effective amount of a mixture of two 2',5' oligoadenylates of claim 1, wherein one of said 2',5' oligoadenylates has a OH group as $R_2$ and a OH as $R_3$, and wherein the other of said 2',5' oligoadenylates has a $PO_4^{2-}$ group as $R_2$ and a OH group as $R_3$.

3. The method for treating diseases and symptoms caused by papillomaviruses in a subject in need of such treatment comprising administering a pharmaceutically effective amount of one or more of the compounds of claim 1, wherein $R_2$ is OH and $R_3$ is OH.

* * * * *